United States Patent [19]

Kubo et al.

[11] 4,393,246

[45] Jul. 12, 1983

[54] PROCESS FOR BROMINATING SIDE CHAIN OF M-PHENOXYTOLUENE

[75] Inventors: Masashige Kubo, Tokuyama; Mitsuaki Yoshimitsu; Kanzi Katsuragawa, both of Shin-nanyo, all of Japan

[73] Assignee: Toyo Soda Manufacturing Co., Ltd., Yamaguchi, Japan

[21] Appl. No.: 316,448

[22] Filed: Oct. 29, 1981

[30] Foreign Application Priority Data

Nov. 21, 1980 [JP] Japan .................................. 55-163360

[51] Int. Cl.³ .............................................. C07C 41/22
[52] U.S. Cl. .................................................... 568/639
[58] Field of Search ........................................ 568/639

[56] References Cited

U.S. PATENT DOCUMENTS 4,302,306 11/1981 Katsuragawa et al. ........ 568/639 X

OTHER PUBLICATIONS

Groggins, Unit Processes in Organic Synthesis (1958) 205.
Prinsloo, J. Catalysis, vol. 32 (1974) 466–469.

*Primary Examiner*—Bernard Helfin
*Attorney, Agent, or Firm*—Oblon, Fisher, Spivak, McClelland & Maier

[57] ABSTRACT

A side chain of m-phenoxytoluene is brominated with a polyhalogenated ethane having the formula

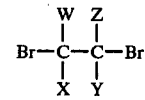

wherein W and Z respectively represent Cl or Br and X and Y respectively represent Cl, Br or H, as a brominating agent in a liquid phase in the presence of an amorphous carbon.

5 Claims, No Drawings

PROCESS FOR BROMINATING SIDE CHAIN OF M-PHENOXYTOLUENE

BACKGROUND OF THE INVENTION

1. Field of the Invention

The present invention relates to a process for brominating a side chain of m-phenoxytoluene by using a polyhalogenated ethane as a brominating agent in the presence of a catalyst of amorphous carbon.

2. Description of the Prior Art m-Phenoxybenzyl bromide and m-phenoxybenzylidene dibromide obtained by brominating a side chain of m-phenoxytoluene can be easily derived into alcohol components of synthetic pyrethroid insecticides which are recently found such as m-phenoxybenzyl alcohol and m-phenoxybenzaldehyde by an esterification followed by a hydrolysis or only hydrolysis or the Sommelet reaction of the product. Therefore, the products are quite useful as intermediates for synthetic pyrethroid insecticides.

It has been reported that a bromination of phenyl nucleus is resulted together with a bromination of the side chain of m-phenoxytoluene in the process for brominating the side chain of m-phenoxytoluene by using bromine as the brominating agent.

The production of phenyl nucleus-brominated compounds causes a reduction of a yield and also causes an industrial trouble in view of difficulty of the separation of the by-products from the side chain brominated compound as the object product.

It has been reported that the bromination of the side chain of m-phenoxytoluene with bromine at 220° C. or higher in the presence of phosphorus halide as described in U.S. Pat. No. 4,014,940 and in the radiation of ultraviolet rays at 180° C. or higher as described in U.S. Pat. No. 4,010,087, in order to reduce the bromination of the phenyl nucleus. Thus, these processes have the disadvantage of producing several percent of the phenyl nucleus-brominated compounds.

The inventors have found that only side chain is selectively brominated without production of the by-products, phenyl nucleus-brominated compounds which are not easily separated, when a polyhalogenated ethane is used as a brominating agent in the bromination of the side chain of m-phenoxytoluene as described in Japanese Patent Application No. 66801/1979. However, the reaction is not resulted at a lower temperature of 150° C. or lower in the process of the bromination by heating without a radical initiator or a radiation of an ultraviolet rays and the reaction is remarkably slow at a temperature of 150° to 180° C. to require a long reaction time to attain high conversion of m-phenoxytoluene. These processes are not economical. In the bromination at 200° C. or higher, the reaction is completed for a short time. However, a special reactor is required for an industrial reaction because of high temperature. The reaction mixture obtained by the bromination is colored in black to produce about 10% of high boiling tar as the by-products. It has been required to attain a bromination of the side chain at lower than 200° C. under a reduction of the side-reactions.

SUMMARY OF THE INVENTION

It is an object of the present invention to improve a bromination of a side chain of m-phenoxytoluene with a polyhalogenated ethane and to reduce side reactions for producing by-products especially phenyl nucleus-brominated compounds.

The foregoing and other objects of the present invention have been attained by providing a process for brominating a side chain of m-phenoxytoluene in a liquid phase with a polyhalogenated ethane having the formula

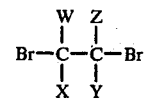

wherein W and Z respectively represent Cl or Br and X and Y respectively represent Cl, Br or H as a brominating agent in the presence of amorphous carbon as a catalyst.

DETAILED DESCRIPTION OF THE PREFERRED EMBODIMENTS

The inventors have studied to improve the bromination of the side chain of m-phenoxytoluene with a polyhalogenated ethane with various catalysts. As a result, it has been found when m-phenoxytoluene is brominated with the polyhalogenated ethane at 100° C. or higher in the presence of the amorphous carbon, reaction is remarkably accelerated to complete the reaction for a short time even at a reaction temperature of 200° C. or lower without the production of phenyl nucleus-brominated compounds and the production of the other by-products and the black coloring of the reaction mixture are reduced. The present invention has been attained by the finding.

It has been known that amorphous carbon especially activated carbon imparts a catalytic effect in a radical reaction. However, the utilization of the amorphous carbon for a bromination of benzyl group has not been considered.

The process of the present invention will be further illustrated.

The present invention is to produce side chain-brominated m-phenoxytoluene by reacting m-phenoxytoluene with a polyhalogenated ethane having the formula

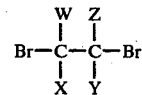

wherein W and Z respectively represent Cl or Br and X and Y respectively represent Cl, Br or H in the presence of amorphous carbon. In accordance with the reaction, polyhalogenated ethylene

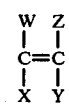

formed by a debromination of the polyhalogenated ethane and hydrogen bromide.

The reaction is as follows:

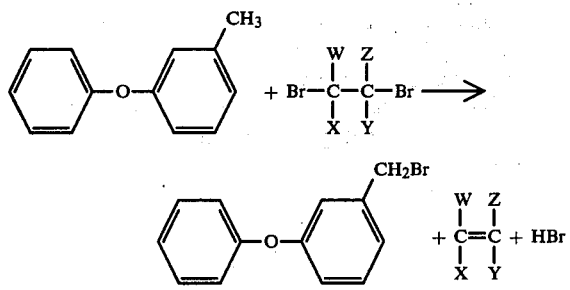

The polyhalogenated ethanes can be 1,2-dibromotetrachloroethane, 1,2-dibromotrichloroethane, 1,1,2,2-tetrabromoethane, pentabromoethane and 1,2-dibromo-1,2-dichloroethane.

It is necessary to use the stoichiometric amount or more of the polyhalogenated ethane. Excess of the polyhalogenated ethane can be used, however, excess of the polyhalogenated ethane should be separated from the product. Thus, the polyhalogenated ethane is preferably two to ten times of the stoichiometric amount.

The compound used as the catalyst is the amorphous carbon such as activated carbon, charcoal, coke and carbon black, especially activated carbon. The form can be powder or granule. An amount of the catalyst can be in a range of 0.01 to 100 wt.% preferably 0.1 to 50 wt.% based on the brominating agent as the reagent.

When the side chain of m-phenoxytoluene is brominated with the polyhalogenated ethane in the presence of amorphous carbon, only side chain is selectively brominated and m-phenoxybenzyl bromide and m-phenoxybenzylidene dibromide can be obtained at high yield.

The reaction temperature is in the range of 100° C. to 270° C. preferably 130° to 250° C.

When any amorphous carbon is not used in the reaction, the reaction is not performed at 150° C. or lower, and the reaction is quite slow at a temperature ranging 150° to 180° C. The bromination is initiated from 100° C. and is performed at a desired reaction velocity at 130° C. or higher when an amorphous carbon is used. When an amorphous carbon is used, the reaction temperature could be reduced for about 50° C. It is considered that the initiation of the thermal decomposition of the polyhalogenated ethane is accelerated by the radical acceptance of the amorphous carbon. In the bromination, it is not necessary to use a solvent, though it is possible to use an inert solvent. The suitable inert solvents can be the solvents which are inert to hydrogen bromide as the by-product and do not adversely affect to the radical reaction and can be chlorobenzene, dichlorobenzene, bromobenzene, and diphenyl ether.

Hydrogen bromide and the polyhalogenated ethylene as the by-products can be distilled off under the atmospheric pressure in the reaction at a temperature of higher than a boiling point of polyhalogenated ethylene, and the brominated m-phenoxytoluene can be remained in the reactor. The same operation can be performed under a reduced pressure.

The bromination of the present invention is selectively performed for the side chain without a bromination of phenyl nucleus. In the side chain, the bromination is sequentially performed in higher degree to produce m-phenoxybenzyl bromide, m-phenoxybenzylidene dibromide and m-phenoxybenzylidine tribromide in the order. The selectivity in the sequential reaction is superior to those of the bromination with bromine. The brominated degree of m-phenoxytoluene can be controlled so as to increase the selectivity. When any amorphous carbon is not used, the reaction mixture obtained by the bromination is colored in black. The high boiling tar is produced at a ratio of about 10% based on the brominated mixture. In the bromination in the presence of the amorphous carbon, the coloring is low and the production of the high boiling tar can be reduced to be a half.

The resulting m-phenoxybenzyl bromide can be easily esterified in a solvent such as acetic acid to produce m-phenoxybenzyl acetate. The product can be easily converted into m-phenoxybenzyl alcohol by a hydrolysis with a base in a solvent such as methanol. In accordance with the aforementioned treatment, m-phenoxybenzylidene dibromide is converted into m-phenoxybenzaldehyde. Thus, m-phenoxybenzyl acetate and m-phenoxybenzaldehyde are produced by the treatment of the mixture of m-phenoxybenzyl bromide and m-phenoxybenzylidene dibromide, m-phenoxybenzyl acetate and m-phenoxybenzaldehyde can be separated from the mixture by a distillation under a reduced pressure.

In accordance with the present invention, m-phenoxybenzyl alcohol and m-phenoxybenzaldehyde can be economically produced by using the side chain-brominated m-phenoxytoluenes obtained at high yield, as intermediates for various synthesis.

The present invention will be further illustrated by certain examples and references which are provided for purposes of illustration only and are not intended to be limiting the present invention.

EXAMPLE 1

Into a 200 ml four necked flask equipped with a distillation column, 36.9 g (0.2 mole) of m-phenoxytoluene and 1.0 g of powdery activated carbon were charged and heated at 180° C. while stirring and then, 71.1 g of 1,2-dibromotrichloroethane (0.24 mole) was added dropwise for 30 minutes and the reaction was continued at the temperature for 3 hours. After the reaction, the reaction mixture was analyzed by a gas chromatography, 1,2-dibromotrichloroethane disappeared, and the production of 27.5 g of m-phenoxybenzyl bromide and 20.2 g of m-phenoxybenzylidene dibromide were found. A conversion of m-phenoxytoluene was 83.7% and a selectivity to total of m-phenoxybenzyl bromide and m-phenoxybenzylidene dibromide was 97.6%. Any phenyl nuclear substituent was not found.

Condition in gas chromatography

Apparatus: Shimazu GC5A
Packed filler: Silicone DC 550 20%, Celite 545 60/80 mesh
Column: Gas column diameter, 3 mm, length 2 m
Condition for measurement: Inlet temperature 200° C.
Column temperature: 200° C.
Carrier gas: He 1.0 Kg/Cm$^2$

REFERENCE 1 m-Phenoxytoluene (460 g: 2.5 mole) was heated at 180° C. and 1,2-dibromotrichloroethane (872 g: 3.0 mole) was added during 8 hours and the reaction was continued at 180° C. until non-detection of 1,2-dibromotrichloroethane. It took 27 hous. After the reaction, the reaction mixture contained 379 g of m-phenoxybenzyl bromide and 171 g of m-phenoxybenzylidene dibromide. A conversion of m-phenoxytoluene was 88.4%. A total selectivity to m-phenoxybenzyl bromide and m-phenoxybenzylidene dibromide from m-phenoxytoluene was 87.5%.

EXAMPLE 2

Into 36.9 g of m-phenoxytoluene, 0.2 g of powdery activated carbon and 60.1 g of 1,2-dibromotrichloroethane were added and the mixture was stirred at 180° to 185° C. for 8 hours. After the reaction, the reaction mixture did not contain 1,2-dibromotrichloroethane, but contained 7.8 g of m-phenoxytoluene, 24.3 g of m-phenoxybenzyl bromide and 12.5 g of m-phenoxybenzylidene dibromide. A conversion of m-phenoxytoluene was 78.8% and a total selectivity to m-phenoxybenzyl bromide and m-phenoxybenzylidene dibromide from m-phenoxytoluene was 81.9%. Any phenyl nuclear substituent was not found.

EXAMPLE 3

In a 1 liter four necked flask equipped with a distillation column, 185 g of m-phenoxytoluene and 5.1 g of powdery activated carbon were charged and the mixture was heated while stirring at 185° to 190° C. Then, 589 g of 1,2-dibromotrichloroethane was added during 2 hours. The reaction was continued at the same temperature until non-detection of 1,2-dibromotrichloroethane. It took 3.5 hours. After the reaction, the reaction mixture did not contain m-pheoxytoluene, but contained 31.4 g of m-phenoxybenzyl bromide and 263 g of m-phenoxybenzylidene dibromide.

A total selectivity to m-phenoxybenzyl bromide and m-phenoxybenzylidene dibromide from m-phenoxytoluene was 88.0%. Any phenyl nuclear substituent was not found. The distilled solution contained 234 g of trichloroethylene, 20 g of 1,2-dibromotrichloroethane and 155 g of hydrogen bromide.

EXAMPLE 4

A mixture of 36.9 g of m-pheoxytoluene and 1.0 g of powdery activated carbon and 72.4 g of 1,2-dibromotrichloroethane was stirred at 170° to 174° C. for 7 hours. After the reaction, the reaction mixture did not contain 1,2-dibromotrichloroethane, but contained 5.2 g of m-phenoxytoluene 15.9 g of m-phenoxybenzyl bromide and 31.1 g of m-phenoxybenzylidene dibromide.

A conversion of m-phenoxytoluene was 85.8%. A total selectivity to m-phenoxybenzyl bromide and m-phenoxybenzylidene dibromide from m-phenoxytoluene was 88.2%. Any phenyl nuclear substituent was not found.

We claim:

1. In a process for brominating a side chain of m-phenoxytoluene with a polyhalogenated ethane having the formula

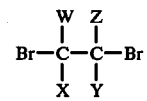

wherein W and Z respectively represent Cl or Br and X and Y respectively represent Cl, Br or H, as a brominating agent, the improvement consisting of carrying out said bromination in the liquid phase in the presence of an amorphous carbon.

2. The process according to claim 1 wherein said bromination is carried out at 100° to 270° C.

3. The process according to claim 1 wherein said bromination is carried out at 130° to 250° C.

4. The process according to claim 1 wherein said amorphous carbon is activated carbon.

5. The process according to claim 1 wherein said bromination is carried out in an inert solvent of chlorobenzene, dichlorobenzene, bromobenzene or diphenyl ether.

* * * * *